(12) United States Patent
Chee et al.

(10) Patent No.: US 6,514,911 B1
(45) Date of Patent: Feb. 4, 2003

(54) SUBSTITUTED OXADIAZINES USEFUL AS PESTICIDES

(75) Inventors: Gaik-Lean Chee, Guelph (CA); Arthur D. Brewer, Puslinch (CA); Allyn R. Bell, Cheshire, CT (US); Alexsei Yurievich Aksinenko, Moscow Region (RU); Vladimir Borisovich Sokolov, Moscow Region (RU)

(73) Assignee: Uniroyal Chemical Company, Inc., Middlebury, CT (US)

( * ) Notice: Subject to any disclaimer, the term of this patent is extended or adjusted under 35 U.S.C. 154(b) by 0 days.

(21) Appl. No.: 10/046,387

(22) Filed: Jan. 16, 2002

(51) Int. Cl.[7] ................................................. A01N 43/72
(52) U.S. Cl. ..................................... 504/223; 514/229.2
(58) Field of Search ..................... 504/223; 514/229.2; 544/67

(56) References Cited

U.S. PATENT DOCUMENTS

| | | | |
|---|---|---|---|
| 2,547,724 A | | 4/1951 | Sundholm .................... 167/33 |
| 2,614,916 A | | 10/1952 | Hoffman et al. .............. 71/2.4 |
| 4,493,728 A | * | 1/1985 | Pilgram .......................... 71/92 |
| 4,561,877 A | * | 12/1985 | Aoki et al. .................... 71/90 |

OTHER PUBLICATIONS

Kryukov et al. (Zh. Vses. Khim. O–Va 1979 24(4) 393–5, chem. abs. 91, 193269e.

* cited by examiner

Primary Examiner—S. Mark Clardy
(74) Attorney, Agent, or Firm—Daniel Reitenbach

(57) ABSTRACT

A method of controlling pests is disclosed wherein the method comprises contacting said pests with an effective amount of a pesticide comprising a composition comprising:

A) a compound of the formula:

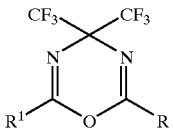

wherein $R^1$ is a straight-chain perfluoroalkyl group or a partially fluorinated straight-chain alkyl group and R is a phenyl group or a substituted phenyl group having at least one substituent, wherein the substituent is selected from the group consisting of amino, formyl, halo, alkyl, alkoxy, haloalkyl, haloalkoxy, and nitro; and B) a suitable carrier therefor.

In a preferred embodiment, the pesticide is a herbicide.

10 Claims, No Drawings

SUBSTITUTED OXADIAZINES USEFUL AS PESTICIDES

BACKGROUND OF THE INVENTION

1. Field of the Invention

The present invention is directed to a class of substituted oxadiazines that are useful as herbicides and, in some cases, as insecticides as well. Hereinafter, the term "pesticide" will be employed as being generic to herbicides, insecticides, nematocides, and miticides. 2. Description of Related Art Undesirable, uncultivated plants—often characterized simply as "weeds"—are able to reduce yields of cultivated plants and other useful agricultural crops by competing with to cultivated plants. As a result, weeds interfere with the growth of seeds, vegetables, fruits, and foliage. Weeds are able to cause this sort of undesirable result because of the tendency of weeds to compete aggressively with cultivated plants for available light and space, moisture, and nutrients in the soil. Furthermore, and as is well-known to those skilled in the crop-protection art, various commercially important food plants as well as plants that are used for structural and ornamental purposes are yet additionally vulnerable to the devastation caused by insect pests.

Weed control is essential for maximum production of many agronomic and horticultural crops including corn (*Zea mays* L.), cotton (Gossypium SP), sunflower (*Helianthus annus* L.), and soybeans (*Glycine max* (L.) Merr.). Weeds on noncropped areas may cause a fire hazard, undesirable drifting of sand or snow, and/or irritation to persons with allergies. Thus, suppression of undesirable weed growth is very advantageous.

Kryukov et al. (Zh. Vses. Khim. O-Va 1979 24(4) 393–5), Chem. Abs. 91, 193269e) describe the preparation of 2-heptafluoropropyl-6-phenyl-4,4-bis(trifluoromethyl)-4H-1,3,5-oxadiazine, but no biological activity or use was disclosed.

The following compounds that are useful in the practice of the present invention are known to be commercially available, but no biological activity is known to have been disclosed: 2-(3-chlorophenyl)-4,4,6-tris(trifluoromethyl)-4H-1,3,5-oxadiazine; 2-(2-chlorophenyl)-6-(pentafluoroethyl)-4,4-bis(trifluoromethyl)-4H-1,3,5-oxadiazine; 2-(pentafluoroethyl)-6-{4-(trifluoromethoxy)phenyl}-4,4-bis(trifluoromethyl)-4H-1,3,5-oxadiazine; and 2-(3,5-dichlorophenyl)-6-(pentafluoroethyl)-4,4-bis(trifluoromethyl)-4H-1,3,5-oxadiazine.

SUMMARY OF THE INVENTION

It has now been found that a particular class of substituted oxadiazines unexpectedly provides excellent pre-emergence and postemergence herbicidal properties and, in some cases, also provides insecticidal properties.

The present invention relates to and has as an object the use of particular 1,3,5-oxadiazines for combating undesirable plant growth, including noxious weeds in agricultural crops. Further objects will become apparent from a study of the present specification and accompanying examples.

More particularly, the present invention is directed to a method of controlling pests comprising contacting said pests with an effective amount of a pesticide comprising a composition comprising:

(A) a compound of the formula:

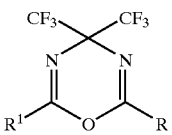

wherein $R^1$ is a straight-chain perfluoroalkyl group or a partially fluorinated straight-chain alkyl group and R is a phenyl group or a substituted phenyl group having at least one substituent, wherein the substituent is selected from the group consisting of amino, formyl, halo, alkyl, alkoxy, haloalkyl, haloalkoxy, and nitro, and (B) a suitable carrier therefor.

In a preferred embodiment, the present invention is directed to a method of controlling unwanted plant life in a location where such control is desirable by application of a herbicidally effective amount of a composition comprising:

(A) a compound of the formula:

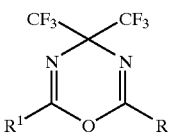

where $R^1$ is a straight-chain perfluoroalkyl group or a partially fluorinated straight-chain alkyl group and R is a phenyl group or a substituted phenyl group having at least one substituent, wherein the substituent is selected from the group consisting of amino, formyl, halo, alkyl, alkoxy, haloalkyl, haloalkoxy, and nitro; and (B) a suitable carrier therefor.

DESCRIPTION OF THE PREFERRED EMBODIMENTS

The present invention is directed to the use of 2-aryl-4,4-bis(trifluoromethyl)-6-fluoroalkyl-4H-1,3,5-oxadiazines having the structural formula:

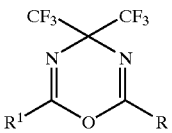

wherein R is an aryl (group, optionally substituted with one or more groups chosen independently from amino, formyl, halo (i.e., fluoro, chloro, or bromo), alkyl, alkoxy, haloalkyl, haloalkoxy or nitro, and $R^1$ is a straight-chain perfluoroalkyl group or a partially fluorinated straight-chain alkyl group.

The compounds employed in the practice of the present invention can be made by the action of an aryl cyanide of formula RCN, where R is as above defined, with a fluorinated alkylidene amide of formula $(CF_3)_2C=NCOR^1$, where $R^1$ is as above defined, in a solvent, such as diethyl ether, allowing the reaction mixture to stand for several hours without heating, then removing the solvent and purifying the product by distillation, chromatography, or crystallization, as appropriate.

The chemical compounds useful as pesticides are bis(4,4-trifluoromethyl)-4H-1,3,5-oxadiazines of the structural formula:

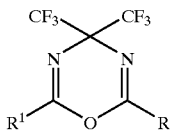

wherein R is a phenyl group, or a phenyl group independently substituted with one or more groups chosen from amino, formyl, halo (fluoro, chloro, or bromo), alkyl, alkoxy, haloalkyl, haloalkoxy, or nitro and $R^1$ is a straight-chain perfluoroalkyl group of from one to three carbon atoms, or a partially fluorinated straight-chain alkyl group. Where a substituent on the phenyl group, R, is alkyl, alkoxy, haloalkyl, or haloalkoxy, it is preferred that the alkyl moiety be a lower alkyl moiety, more preferably a lower alkyl of from one to four carbon atoms, e.g., methyl, ethyl, propyl, isopropyl, butyl, isobutyl, sec-butyl, or tert-butyl, and most preferred that it be methyl.

Representative sets of values for such compounds are given in Table 1, where for clarity the substituents on the phenyl ring are separately specified as $R^2$ and $R^3$.

TABLE 1

| Cmpd# | $R^1$ | $R^2$ | $R^3$ |
|---|---|---|---|
| 1 | $CF_3$ | H | H |
| 2 | $CF_3$ | 4-Br | H |
| 3 | $CF_3$ | 2-F | H |
| 4 | $CF_3$ | 3-Cl | H |
| 5 | $CF_3$ | 4-Cl | H |
| 6 | $CF_3$ | 2-$CF_3$ | H |
| 7 | $CF_3$ | 3-$CF_3$ | H |
| 8 | $CF_3$ | 4-$CF_3O$ | H |
| 9 | $CF_3$ | 4-$NH_2$ | H |
| 10 | $CF_3$ | 4-$NO_2$ | H |
| 11 | $CF_2CF_3$ | H | H |
| 12 | $CF_2CF_3$ | 2-Cl | H |
| 13 | $CF_2CF_3$ | 3-Cl | H |
| 14 | $CF_2CF_3$ | 3-$CF_3$ | H |
| 15 | $CF_2CF_3$ | 4-$CF_3$ | H |
| 16 | $CF_2CF_3$ | 4-$CF_3O$ | H |
| 17 | $CF_2CF_3$ | 4-F | H |
| 18 | $CF_2CF_3$ | 3-$CF_3$ | 5-$CF_3$ |
| 19 | $CF_2CF_3$ | 3-F | 5-F |
| 20 | $CF_2CF_3$ | 3-Cl | 4-F |
| 21 | $CF_2CF_3$ | 3-Cl | 5-Cl |
| 22 | $CF_2CF_3$ | 3-$CH_3$ | H |
| 23 | $CF_2CF_3$ | 3-$CH_3O$ | H |
| 24 | $CF_2CF_3$ | 4-Cl | H |
| 25 | $CF_2CF_3$ | 4-Br | H |
| 26 | $CF_2CF_2CF_3$ | 3-Cl | H |
| 27 | $CF_2CF_2CF_3$ | 4-Br | H |
| 28 | $CF_2CF_2CF_3$ | 4-F | H |
| 29 | $CF_2CF_2CF_3$ | 3-$CF_3$ | H |
| 30 | $CF_2CF_2CF_3$ | 4-$CH_3$ | H |
| 31 | $CF_2CF_2CF_3$ | 4-CHO | H |
| 32 | $CHF_2$ | 3-$CF_3$ | H |
| 33 | $CHF_2$ | 4-$CF_3$ | H |

Chemicals of the foregoing, class include:
1 2-phenyl-4,4,6-tris(trifluoromethyl)-4H-1,3,5-oxadiazine;
2 2-(4-bromophenyl)-4,4,6-tris(trifluoromethyl)-4H-1,3,5-oxadiazine;
3 2-(2-fluorophenyl)-4,4,6-tris(trifluoromethyl)-4H-1,3,5-oxadiazine;
4 2-(3-chlorophenyl)-4,4,6-tris(trifluoromethyl)-4H-1,3,5-oxadiazine,
5 2-(4-chlorophenyl)-4,4,6-tris(trifluoromethyl)-4H-1,3,5-oxadiazine;
6 2,4,4-tris(trifluoromethyl)-6-{(2-trifluoromethyl)phenyl}-4H-1,3,5-oxadiazine;
7 2,4,4-tris(trifluoromethyl)-6-{(3-trifluoromethyl)phenyl}-4H-1,3,5-oxadiazine;
8 2-{4-(trifluoromethoxy)phenyl}-4,4,6-tris(trifluoromethyl)-4H-1,3,5-oxadiazine;
9 2-(4-aminophenyl)-4,4,6-tris(trifluoromethyl)-4H-1,3,5-oxadiazine;
10 2-(4-nitrophenyl)-4,4,6-tris(trifluoromethyl)-4H-1,3,5-oxadiazine;
11 2-(pentafluoroethyl)-6-phenyl-4,4-bis(trifluoromethyl)-4H-1,3,5-oxadiazine;
12 2-(2-chlorophenyl)-6-(pentafluoroethyl)-4,4-bis(trifluoromethyl)-4H-1,3,5-oxadiazine;
13 2-(3-chlorophenyl)-6-(pentafluoroethyl)-4,4-bis(trifluoromethyl)-4H-1,3,5-oxadiazine;
14 2-(pentafluoroethyl)-4,4-bis(trifluoromethyl)-6-{(3-trifluoromethyl)phenyl}-4H-1,3,5-oxadiazine;
15 2-(pentafluoroethlyl)-4,4-bis(trifluoromethyl)-6-{4-trifluoromethyl)phenyl}-4H-1,3,5-oxadiazine;
16 2-(pentafluoroethyl)-6-{(4-trifluoromethoxy)phenyl}-4,4-bis(trifluoromethyl)-4H-1,3,5-oxadiazine;
17 2-(4-fluorophenyl)-6-(pentafluoroethyl)-4,4-bis(trifluoromethyl)-4H-1,3,5-oxadiazine;
18 2-{3,5-bis(trifluoromethyl)phenyl}-6-(pentafluoroethyl)-4,4-bis(trifluoromethyl)-4H-1,3,5-oxadiazine;
19 2-(3,5-difluorophenyl)-6-(pentafluoroethyl)-4,4-bis(trifluoromethyl)-4H-1,3,5-oxadiazine;
20 2-(3-chloro-4-fluorophenyl)-6-(pentafluoroethyl)-4,4-bis(trifluoromethyl)-4H-1,3,5-oxadiazine;
21 2-(3,5-dichlorophenyl)-6-(pentafluoroethyl)-4,4-bis(trifluoromethyl)-4H-1,3,5-oxadiazine;
22 2-(3-methylphenyl)-6-(pentafluoroethyl)-4,4-bis(trifluoromethyl)-4H-1,3,5-oxadiazine;
23 2-(3-methoxyphenyl)-6-(pentafluoroethyl)-4,4-bis(trifluoromethyl)-4H-1,3,5-oxadiazine;
24 2-(4-chlorophenyl)-6-(pentafluoroethyl)-4,4-bis(trifluoromethyl)-4H-1,3,5-oxadiazine;
25 2-(4-bromophenyl)-6-(pentafluoroethyl)-4,4-bis(trifluoromethyl)-4H-1,3,5-oxadiazine;
26 2-(3-chlorophenyl)-6-(heptafluoropropyl)-4,4-bis(trifluoromethyl)-4H-1,3,5-oxadiazine;
27 2-(4-bromophenyl)-6-(heptafluoropropyl)-4,4-bis(trifluoromethyl)-4H-1,3,5-oxadiazine;
28 2-(4-fluorophenyl)-6-(heptafluoropropyl)-4,4-bis(trifluoromethyl)-4H-1,3,5-oxadiazine;
29 2-(heptafluoropropyl)-4,4-bis(trifluoromethyl)-6-{(3-trifluoromethyl)phenyl}-4H-1,3,5-oxadiazine;
30 2-(heptafluoropropyl)-4,4-bis(trifluoromethyl)-6-{(4-trifluoromethyl)phenyl}-4H-1,3,5-oxadiazine;
31 4-{6-(pentafluoroethyl)-4,4-bis(trifluoromethyl)-4H-1,3,5-oxadiazin-2-yl}-benzaldehyde;
32 2-(difluoromethyl)-4,4-bis(trifluoromethyl)-6-(3-trifluoromethylphenyl)-4H-1,3,5-oxadiazine; and
33 21-(dfluoromethyl)-4,4-bis(trifluoromethyl)-6-(4-trifluoromethylphenyl)-4H-1,3,5-oxadiazine.

Compositions useful in the practice of the present invention include herbicidal compositions, insecticidal compositions, miticidal compositions, and nematocidal compositions (collectively referred to herein simply as "pesticidal compositions"). Such a pesticidal composition comprises:

(A) a pesticidally effective amount of at least one compound having the structural formula presented and defined above, and (B) a suitable carrier therefor.

The present invention is directed to a method for controlling undesirable populations of weeds, insects, mites, and nematodes, utilizing at least one compound having the structural formula presented and defined above.

Such a method comprises applying to a pre-selected site or "locus" a pesticidally effective amount of a composition comprising:

(A) a pesticidally effective amount of at least one compound having the structural formula presented and defined above; and (B) a suitable carrier therefor.

As stated above the composition employed in the practice of the present pesticidal invention includes, as one component thereof, a carrier suitable for admixture with the active ingredient of the present invention. The identity and type of carrier that would be suitable for such purposes may be selected according to the following criteria.

In certain applications, a suitable carrier might take the form of a finely divided particulate solid, or granules, or pellets; or it might take the form of a wettable powder, a flowable liquid, or a soluble powder, while in yet other applications the carrier might take the form of an aqueous or organic solvent, an aqueous or organic dispersant, or an aqueous or organic emulsifying agent.

Among those materials that may be utilized to produce a suitable solid carrier (e.g., a carrier taking the form of pellets, granules, wettable powders, soluble powders, other finely divided particles, and the like) are such well-known commercially available materials as attapulgite clay, sand, vermiculite, corn cobs, activated carbon, and mineral silicates such as mica, talc, pyrophyllite, and the like.

Where the carrier is a solid, a biologically-active solid composition can readily be prepared utilizing the active ingredient of the present invention. For example, the active ingredient can be impregnated onto the solid carrier, as those skilled in the art can well appreciate. Alternatively, the active ingredient of the present invention may be formulated into a wettable powder by grinding a suitable compound form of the active ingredient into a fine powder, and thereafter mixing or otherwise combining the resulting powder with a suitable solid carrier into which a suitable surface-active dispersing agent has been added. The resulting wettable powder may then be dispersed in water and thereafter sprayed onto soil surfaces, crops to be protected, and/or weeds.

In the case where the carrier is a liquid, a biologically active liquid composition can readily be prepared utilizing the active ingredient of the present invention. In particular, a liquid solution is representative of a preferred embodiment of such a liquid composition.

In the case of a liquid solution, the active compound may readily be dissolved in a suitable aqueous or organic solvent, as can easily be appreciated by those skilled in the art. Among the preferred solvents employed in the practice of the present invention are aromatic or aliphatic hydrocarbons. Of the hydrocarbons, toluene is particularly preferred.

Within the contemplation of our present invention, however, liquid emulsions are more commonly employed than are liquid solutions. Accordingly, biologically active formulations which include the active ingredient of our present invention would—most likely—utilize one of the most plentiful and cost-effective carriers known to man, water. For these and other reasons water is a preferred carrier.

Yet another carrier is a combination of solvent and water. In this embodiment a compound of this invention is dissolved in a solvent, such as benzene, toluene, or other aliphatic or aromatic hydrocarbon. An emulsifiable concentrate is formed with the addition of a surface active and/or dispersing agent. The emulsifiable concentrate is then dispersed in water. In this composition, water solubility may be increased using a co-solvent system involving acetone, dimethyl sulfoxide, or other water miscible solvent. The resulting aqueous emulsion may thereafter advantageously be applied to a particular location (i.e., "locus") to be protected, a particularly preferred method of application being spraying.

The surface-active dispersing agent may be any of those known to those skilled in the art. In addition, suitable surface-active agents for use in the composition of this invention are known to those skilled in the art. In addition, suitable surface active agents for use in the composition of this invention are provided in McCutcheon's Detergents and Emulsifiers, 1999, The Manufacturing Confectioner Publishing Co., Glen Rock, N.J. U.S. Pat. No. 2,614,916, columns 2 to 4; and U.S. Pat. No. 2,547,724, columns 3 and 4.

In addition to the active ingredient and the carrier, the compositions employed in the practice of the present invention can also comprise one or more of the formulating agents well known to those skilled in the art.

With respect to still another aspect of our present invention, a method for controlling weeds and other undesirable vegetation as well as insect pests (including mites and nematodes) shall now be discussed. In particular, such a method preferably comprises applying an effective amount of the biologically active ingredient having the above described structural formula to a pre-selected location (i.e., "locus") which is to be protected. As was also mentioned above, the biologically active ingredient may advantageously be combined with a suitable carrier to produce a particular formulation which, in turn, is applied to a particular locus.

In the case where the composition comprises impregnated granules of the compound of this invention, the preferred means of application for weed control is by spreading it on the soil. The wettable powder may be similarly applied. In the case where the wettable powder is dispersed in water, this composition controls weeds by spraying the dispersion on weeds or unwanted vegetation or onto the soil surface. Where an emulsion is formed, that emulsion is likewise sprayed onto the weeds or onto the soil surface.

When employed as a herbicide, the concentration of the active ingredient in the composition of this invention may vary widely, e.g., from 1 to 95 percent. The concentration of active compound in dispersions applied to the soil or foliage is generally from 0.002 percent to about 75 percent.

For use as a pre-emergence herbicide, the active ingredient is typically applied at rates of from about 0.05 to about 25 pounds per acre (from about 0.056 to about 28 kg/ha) to soil that contains weed and crop seed, namely either to the surface of the soil or incorporated into the upper one to three inches (2.5 to 7.5 cm.) of soil. As a postemergence herbicide, the active ingredient is typically applied at rates of from about 0.05 to about 25 pounds per acre (from about 0.056 to about 28 kg/ha) to the foliage of weeds and may be employed singly or as a mixture of two or more chemicals. Post-emergent application may be made by ground or aerial spraying of the undesired vegetation.

When employed as a herbicide, the most suitable rate of application in any given case will depend on such factors as soil type, soil pH, soil organic matter content, the quantity and intensity of rainfall before and after treatment, the air and soil temperature, light intensity, and light duration per day. All of these factors can have an influence on the efficacy of the chemicals for a given weed control use. However, one skilled in the art can, by routine experimentation, readily determine optimum conditions for the employment of any particular compound for use in the practice of this invention.

The herbicide use may include control of vegetation at industrial sites or selective weed control in crop fields.

In addition to their usefulness as herbicides, the following compounds have been found to have insecticidal properties: 2-(pentafluoroethyl)-4,4-bis(trifluoromethyl)-6-{(3-trifluoromethyl)phenyl}-4H-1,3,5-oxadiazine; 2-(pentafluoroethyl)-6-{(4-trifluoromethoxy)phenyl}-4,4-bis(trifluoromethyl)-4H-1,3,5-oxadiazine; and 2-(3-chlorophenyl)-6-(heptafluoropropyl)-4,4-bis(trifluoromethyl)-4H-1,3,5-oxadiazine.

The advantages and the important features of the present invention will be more apparent from the following examples.

EXAMPLES

Example 1

Preparation of 2-(3-Methoxyphenyl)-6-pentafluoroethyl-4,4-bis(trifluoromethyl)-4H-1,3,5-oxadiazine 3-Methoxybenzonitrile (1.31 g. 0.01 mole) and 2,2,3,3,3-pentafluoro-N-{2,2,2-trifluoro-1-(trifluoromethyl)ethylidene}propanamide (4.67 g., 0.015 mole) were dissolved in diethyl ether and heated in a glass ampoule to 60° C. for six hours. Solvent was evaporated off and the residue distilled at 119° to 120° C./13 min to give a colorless oil (361 g, 82 percent). PMR (CDCl$_3$), 3.85 s (3H), 7.18 d (1H), 7.40 t (1H), 7.55 s (1H), 7.65 d (1H), $^{19}$F NMR, −45.74 (2F), −5.47 (3F), −1.12 (6F).

Example 2

Preparation of 2-Pentafluoroethyl-4,4-bis(trifluoromethyl)-6-(3-trifluoromethyl-phenyl)-4H-1,3,5-oxadiazine 3-Trifluoromethylbenzonitrile (1.69 g, 0.01 mole) and 2,2,3,3,3-pentafluoro-N-{2,2,2-trifluoro-1-(trifluoromethyl)ethylidene}propanamide (4.67 g, 0.015 mole) were dissolved in diethyl ether, sealed in an ampoule and kept at 60° C. for six hours. The solvent was evaporated and the residue distilled at reduced pressure to give a colorless oil, 4.4 g. (90 percent). PMR (CDCl$_3$), 7.70 t (1H), 7.95 d (1H), 8.30 s&d (2H); $^{19}$F NMR, −45.68 (2F), −5.49 (3F), −10 (6F), 14.11 (3F).

Example 3

Preparation of 2-(4-Bromophenyl)-6-(heptafluoropropyl)-4,4-bis(trifluoromethyl)-4H-1,3,5-oxadiazine 4-Bromobenzonitrile (0.3 g, 1.65 mmol) and 2,2,3,3,4,4,4-heptafluoro-N-{2,2,2-trifluoro-1-(trifluoromethyl)ethylidene}butanamide (1.2 g, 3.3 mmol) were dissolved in diethyl ether (4.0 mL) and heated in a sealed glass tube to 60° C. for 17 hours. The solvent and excess reagent were distilled off to give a colorless liquid (0.9 g, 100 percent yield). EIMS (m/z): 543 (M$^+$), 524 (M−F), 474 (M−CF$_3$).

Example 4

Preparation of 2,4,4-Tris(trifluoromethyl)-6-{3-(trifluoromethyl)phenyl}-4H-1,3,5-oxadiazine 3-Trifluoromethylbenzonitrile (5.8 g, 3.39 mmol) and 2,2,2-trifluoro-N-{2,2,2-trifluoro-1-(trifluoromethyl)ethylidene}acetamide (1.8 g, 6.90 mmol) were dissolved in dichloromethane (3 mL) and stirred in a sealed vial at room temperature for three days. The solvent and excess reagent were distilled off to give a colorless oil that was chromatographed on silica gel using 5 percent ethyl acetate/hexanes as eluent. The desired product was present as an oil (0.92 g, 63 percent yield) in the first eluted fraction. EIMS (m/z): 432 (M$^+$), 413 (M−F), 363 (M−CF$_3$).

Example 5

To illustrate the effectiveness of the previously described substituted oxadiazines of this invention as preemergence herbicides, 300 mg of the chemical was dissolved in a composition comprising 10 mL acetone to which 30 mg of tile emulsifying agent, ethoxylated sorbitan monolaurate, was added. The solution was diluted to 100 mL with distilled water. Ten milliliters of this 3000 ppm solution was diluted to 250 ppm with distilled water. The chemical was applied at the rate of 10 pounds/acre (11.2 kg/ha) by drenchings 46 mL of the 250 ppm solution on the surface of soil in 4½ inch (11.25 cm) plastic pots wherein seeds of the following weeds had been planted:

velvetleaf (*Abutilon theophrasti* Medik.) (VL), jimsonweed (*Datura stramonium* L.) (JW), prickly sida (*Sida spinosa* L.) (PS), tall morningglory (*Ipomoea purpurea* (L.) Roth) (TM), switchgrass (*Panicum virgahim* L.) (SG), barnyardgrass (*Echinochloa crus-galli* (L.) Beauv.) (BG), and green foxtail (*Setaria virdis* (L.) Beauv.) (GF).

The percent control of the weeds compared to untreated checks was determined two weeks after treatment. TABLE 1 summarizes the results achieved with compounds formulated as indicated above, and the data clearly indicate the good to excellent herbicidal efficacy of compositions of this invention.

TABLE 1

| COMPOUND | Preemergence Activity – Percent Weed Control at 10 lbs/A | | | | | | |
|---|---|---|---|---|---|---|---|
| NO. | VL | JW | PS | TM | BG | SG | GF |
| 1 | 100 | — | 100 | 100 | 0 | 0 | 0 |
| 2 | 100 | — | 100 | 100 | 100 | 100 | 100 |
| 3 | 100 | — | 0 | 0 | 0 | 30 | 40 |
| 4 | 100 | — | 100 | 100 | 100 | 100 | 100 |
| 5 | 100 | 100 | — | 100 | 100 | 100 | 100 |
| 6 | 100 | 75 | — | 100 | 50 | 75 | 100 |
| 7 | 100 | — | 100 | 100 | 100 | 100 | 100 |
| 8 | 100 | — | 100 | 100 | 100 | 100 | 100 |
| 9 | 90 | — | 0 | 0 | 0 | 90 | 90 |
| 10 | 80 | — | 80 | 50 | 80 | 80 | 80 |
| 11 | 100 | — | 100 | 100 | 0 | 0 | 50 |
| 12 | 100 | 100 | — | 100 | 0 | 75 | 100 |
| 13 | 100 | — | 100 | 100 | 100 | 100 | 100 |
| 14 | 100 | 100 | — | 100 | 100 | 100 | 100 |
| 15 | 100 | — | 100 | 100 | 100 | 100 | 100 |
| 16 | 100 | 100 | — | 100 | 100 | 100 | 100 |
| 17 | 100 | — | 100 | 100 | 100 | 50 | 50 |

TABLE 1-continued

| COMPOUND | Preemergence Activity Percent Weed Control at 10 lbs/A | | | | | | |
|---|---|---|---|---|---|---|---|
| NO. | VL | JW | PS | TM | BG | SG | GF |
| 18 | 100 | — | 100 | 100 | 100 | 100 | 100 |
| 19 | 100 | — | 100 | 100 | 100 | 100 | 100 |
| 20 | 100 | — | 100 | 100 | 100 | 100 | 100 |
| 21 | 100 | 100 | — | 100 | 100 | 100 | 100 |
| 22 | 100 | 100 | — | 0 | 0 | 0 | 50 |
| 23 | 100 | 100 | — | 100 | 0 | 50 | 50 |
| 24 | 100 | — | 100 | 100 | 90 | 100 | 100 |
| 25 | 100 | — | 100 | 100 | 90 | 100 | 100 |
| 26 | 100 | 100 | — | 100 | 100 | 100 | 100 |
| 27 | 100 | — | 100 | 95 | 0 | 0 | 0 |
| 28 | 100 | — | 100 | 100 | 0 | 0 | 0 |
| 29 | 100 | — | 100 | 100 | 100 | 100 | 100 |
| 30 | 100 | — | 100 | 100 | 100 | 100 | 100 |
| 31 | — | — | — | — | 100 | — | — |
| 32 | — | — | 100 | — | 80 | 0 | 100 |
| 33 | — | — | 100 | — | 20 | — | 40 |

The application rates for 32 and 33 are 5 lbs/A.

Example 6

Comparative Example

To illustrate the lack of activity of 2-(heptafluoropropyl)-6-phenyl-4,4-bis(trifluoromethyl)-4H-1,3,5-oxadiazine, a prior art compound, and hence the surprising and unexpected nature of the activity of the compositions of the present invention, the corresponding test results at 10 lb/A are given below.

VL/0 JW/0 PS/0 TM/0 BG/0 SG/0 GF/0

Example 7

To illustrate the effectiveness of the described substituted oxadiazines as postemergence herbicides, the 3000 ppm solution described under Example 5 was atomized with a conventional DeVilbiss™ sprayer, wetting the foliage to the drip point. The weeds, which were the same species as described in Example 5, were treated six days after emergence. The percent weed control was evaluated two weeks after treatment. TABLE 2 illustrates the postemergence herbicidal efficacy of compositions of this invention.

TABLE 2

| | Postemergence Activity Percent Weed Control at 3000 ppm | | | | | |
|---|---|---|---|---|---|---|
| COMPOUND NO | VL | PS | TM | BG | SG | GF |
| 4 | 50 | 90 | 100 | 100 | 80 | 100 |
| 13 | 100 | 100 | 100 | 80 | 90 | 100 |
| 20 | 70 | 70 | 0 | 30 | 30 | 0 |
| 24 | 50 | 100 | 0 | 20 | 20 | 0 |
| 25 | 100 | 100 | 20 | 50 | 0 | 30 |

In view of the many changes and modifications that can be made without departing from principles underlying the invention, reference should be made to the appended claims for an understanding of the scope of the protection to be afforded the invention.

What is claimed is:

1. A method of controlling pests comprising contacting said pests with an effective amount of a pesticide comprising a composition comprising:

A) a compound of the formula:

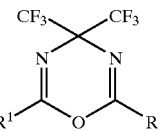

wherein $R^1$ is a straight-chain perfluoroalkyl group or a partially fluorinated straight-chain alkyl group and R is a phenyl group or a substituted phenyl group having at least one substituent, wherein the substituent is selected from the group consisting of amino, formyl, halo, alkyl alkoxy, haloalkyl, haloalkoxy, and nitro; and B) a suitable carrier therefore.

2. A method of controlling unwanted plant life in a location where such control is desirable by application of a herbicidally effective amount of a composition comprising A) a compound of the formula:

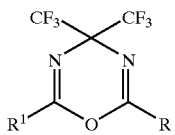

where $R^1$ is a straight-chain perfluoroalkyl group or a partially fluorinated straight-chain alkyl group and R is a phenyl group or a substituted phenyl group having at least one substituent, wherein the substituent is selected from the group consisting of amino, formyl, halo, alkyl, alkoxy, haloalkyl, haloalkoxy, and nitro; and B) a suitable carrier therefor.

3. The method of claim 2 wherein R is of the structure:

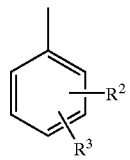

wherein $R^2$ and $R^3$ are independently selected from the group consisting of hydrogen, amino, formyl, halo, alkyl, alkoxy, haloalkyl, haloalkoxy, and nitro.

4. The method of claim 3 wherein $R^1$, $R^2$ and $R^3$ have the following values:

| $R^1$ | $R^2$ | $R^3$ |
|---|---|---|
| $CF_3$ | H | H |
| $CF_3$ | 4-Br | H |
| $CF_3$ | 2-F | H |
| $CF_3$ | 3-Cl | H |
| $CF_3$ | 4-Cl | H |
| $CF_3$ | 2-$CF_3$ | H |
| $CF_3$ | 3-$CF_3$ | H |
| $CF_3$ | 4-$CF_3$O | H |
| $CF_3$ | 4-$NH_2$ | H |
| $CF_3$ | 4-$NO_2$ | H |
| $CF_2CF_3$ | H | H |
| $CF_2CF_3$ | 2-Cl | H |
| $CF_2CF_3$ | 3-Cl | H |
| $CF_2CF_3$ | 3-$CF_3$ | H |
| $CF_2CF_3$ | 4-$CF_3$ | H |
| $CF_2CF_3$ | 4-$CF_3$O | H |

-continued

| R¹ | R² | R³ |
|---|---|---|
| CF₂CF₃ | 4-F | H |
| CF₂CF₃ | 3-CF₃ | 5-CF₃ |
| CF₂CF₃ | 3-F | 5-F |
| CF₂CF₃ | 3-Cl | 4-F |
| CF₂CF₃ | 3-Cl | 5-Cl |
| CF₂CF₃ | 3-CH₃ | H |
| CF₂CF₃ | 3-CH₃O | H |
| CF₂CF₃ | 4-Cl | H |
| CF₂CF₃ | 4-Br | H |
| CF₂CF₂CF₃ | 3-Cl | H |
| CF₂CF₂CF₃ | 4-Br | H |
| CF₂CF₂CF₃ | 4-F | H |
| CF₂CF₂CF₃ | 3-CF₃ | H |
| CF₂CF₂CF₃ | 4-CF₃ | H |
| CF₂CF₃ | 4-CHO | H |
| CHF₂ | 3-CF₃ | H |
| CHF₂ | 4-CF₃ | H |

5. The method of claim 2 wherein the compound is selected from the group consisting of:
2-phenyl-4,4,6-tris(trifluoromethyl)-4H-1,3,5-oxadiazine;
2-(4-bromophenyl)-4,4,6-tris(trifluoromethyl)-4H-1,3,5-oxadiazine;
2-(2-fluorophenyl)-4,4,6-tris(trifluoromethyl)-4H-1,3,5-oxadiazine;
2-(3-chlorophenyl)-4,4,6-tris(trifluoromethyl)-4H-1,3,5-oxadiazine;
2-(4-chlorophenyl)-4,4,6-tris(trifluoromethyl)-4H-1,3,5-oxadiazine;
2,4,4-tris(trifluoromethyl)-6-(2-trifluoromethylphenyl)-4H-1,3,5-oxadiazine;
2,4,4-tris(trifluoromethyl)-6-(3-trifluoromethylphenyl)-4H-1,3,5-oxadiazine;
2-{4-(trifluoromethoxy)phenyl}-4,4,6-tris(trifluoromethyl)-4H-1,3,5-oxadiazine;
2-(4-aminophenyl)-4,4,6-tris(trifluoromethyl)-4H-1,3,5-oxadiazine;
2-(4-nitrophenyl)-4,4,6-tris(trifluoromethyl)-4H-1,3,5-oxadiazine;
2-(pentafluoroethyl)-6-phenyl-4,4-bis(trifluoromethyl)-4H-1,3,5-oxadiazine;
2-(2-chlorophenyl)-6-(pentafluoroethyl)-4,4-bis(trifluoromethyl)-4H-1,3,5-oxadiazine;
2-(3-chlorophenyl)-6-(pentafluoroethyl)-4,4-bis(trifluoromethyl)-4H-1,3,5-oxadiazine;
2-(pentafluoroethyl)-4,4-bis(trifluoromethyl)-6-{(3-trifluoromethyl)phenyl}-4H-1,3,5-oxadiazine;
2-(pentafluoroethyl)-4,4-bis(trifluoromethyl)-6-{(4-trifluoromethyl)phenyl}-4H-1,3,5-oxadiazine;
2-(pentafluoroethyl)-6-(3-trifluoromethoxy)phenyl)-4,4-bis(trifluoromethyl)-4H-1,3,5-oxadiazine;
2-(4-fluorophenyl)-6-(pentafluoroethyl)-4,4-bis(trifluoromethyl)-4H-1,3,5-oxadiazine;
2-{3,5-bis(trifluoromethyl)phenyl}-6-pentafluoroethyl-4,4-bis(trifluoromethyl)-4H-1,3,5-oxadiazine;
2-(3,5-difluorophenyl)-6-(pentafluoroethyl)-4,4-bis(trifluoromethyl)-4H-1,3,5-oxadiazine;
2-(3-chloro-4-fluorophenyl)-6-(pentafluoroethyl)-4,4-bis(trifluoromethyl)-4H-1,3,5-oxadiazine;
2-(3,5-dichlorophenyl)-6-(pentafluoroethyl)-4,4-bis(trifluoromethyl)-4H-1,3,5-oxadiazine;
2-(3-methylphenyl)-6-(pentafluoroethyl)-4,4-bis(trifluoromethyl)-4H-1,3,5-oxadiazine;
2-(3-methoxyphenyl)-6-(pentafluoroethyl)-4,4-bis(trifluoromethyl)-4H-1,3,5-oxadiazine;
2-(4-bromophenyl)-6-(pentafluoroethyl)-4,4-bis(trifluoromethyl)-4H-1,3,5-oxadiazine;
2-(4-bromophenyl)-6-(heptafluoropropyl)-4,4-bis(trifluoromethyl)-4H-1,3,5-oxadiazine;
2-(4-fluorophenyl)-6-(heptafluoropropyl)-4,4-bis(trifluoromethyl)-4H-1,3,5-oxadiazine;
2-(heptafluoropropyl)-4,4-bis(trifluoromethyl)-6-{(3-trifluoromethyl)phenyl}-4H-1,3,5-oxadiazine;
2-(heptafluoropropyl)-4,4-bis(trifluoromethyl)-6-{(4-trifluoromethyl)phenyl}-4H-1,3,5-oxadiazine;
4-{6-(pentafluoroethyl)-4,4-bis(trifluoromethyl)-4H-1,3,5-oxadiazin-2-yl}-benzaldehyde;
2(difluoromethyl)-4,4-bis(trifluoromethylphenyl)-4H-1,3,5-oxadiazine; and difluoromethyl)-4,4-bis(trifluoromethyl)-6-(4-trifluoromethylphenyl)-4H-1,3,5-oxadiazine.

6. The method of claim 1 wherein the composition further comprises at least one formulating agent.

7. The method of claim 2 wherein the composition further comprises at least one formulating agent.

8. The method of claim 3 wherein the composition further comprises at least one formulating agent.

9. The method of claim 4 wherein the composition further comprises at least one formulating agent.

10. The method of claim 5 wherein the composition further comprises at least one formulating agent.

* * * * *